United States Patent [19]  [11] 4,320,117
Dutta et al.  [45] Mar. 16, 1982

[54] POLYPEPTIDE

[75] Inventors: Anand S. Dutta; James J. Gormley; Christopher F. Hayward; John S. Morley; Gilbert J. Stacey, all of Macclesfield, England

[73] Assignee: Imperial Chemical Industries Limited, London, England

[21] Appl. No.: 799,938

[22] Filed: May 24, 1977

[30] Foreign Application Priority Data

Jun. 21, 1976 [GB] United Kingdom ............... 25642/76
Oct. 28, 1976 [GB] United Kingdom ............... 44839/76

[51] Int. Cl.³ ..................... A61K 37/00; C07C 103/52
[52] U.S. Cl. .............................. 424/177; 260/112.5 E
[58] Field of Search .................. 424/177; 260/112.5 R

[56] References Cited

U.S. PATENT DOCUMENTS 4,038,222  7/1977  Li .................................... 424/177

OTHER PUBLICATIONS

A. J. Kastin et al., Brain Res. Bull., 1, pp. 583–589, 1976.
C. Pert et al., Opiates and Endogenous Opioid Peptides, pp. 79–86, 1976.
J. M. Walker et al., Science 196, pp. 85–87, 1977.
N. P. Plotnikoff et al., Life Sciences 19, pp. 1283–1288, 1976.
C. Pert, Science 194, 1976, pp. 330–332.
A. Kastin et al., Pharm. Biochem. & Behavior 5, pp. 691–695, 1976.
D. H. Coy et al., Biochem. and Biophys. Res. Comm. 73, 1976, pp. 632–638.
A. F. Bradbury et al., Nature 260, 1976, pp. 793–795.

*Primary Examiner*—Delbert R. Phillips
*Attorney, Agent, or Firm*—Cushman, Darby & Cushman

[57] ABSTRACT

The disclosure relates to novel polypeptides which possess analgesic activity, to processes for their manufacture and to pharmaceutical compositions containing them. Typical of the peptides disclosed is:

H-Tyr-D-Ala-Gly-Phe-Leu-Thr-Ser-Glu-Lys
Ser-Gln-Thr-Pro-Leu-Val
Thr-Leu-Phe-Lys-Asn-
Ala-Ile-Val-Lys-Asn-Ala-His-Lys-Lys-Gly-Gln-OH

7 Claims, No Drawings

POLYPEPTIDE

This invention relates to polypeptides which possess analgesic properties.

It is known that residues 61–91 of the naturally-occurring lipolytic polypeptide hormone lipotropin (now known as the C-fragment of lipotropin, or β-endorphin) possesses analgesic properties when injected directly into the 3rd ventricle of the cat. (A. F. Bradbury et al., *Nature*, 1976, 260, 793). It has now been found that when the glycine at position 62 is replaced by a D-amino-acid residue, compounds having analgesic activity when dosed intravenously on a standard analgesic test system are produced.

According to the invention there is provided a polypeptide of the formula:

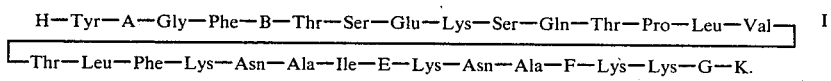

in which A stands for D-Ala, D-Ser or D-Met, B stands for Leu or Met, E stands for Val or Ile, F stands for His or Tyr, G stands for Gly-Gln, Gly-Glu or for a direct bond, and K stands for a hydroxy or amino radical or an alkoxy radical of 1 to 6 carbon atoms; and the pharmaceutically-acceptable acid-addition salts thereof, and, where the polypeptide of the formula I contains a free carboxy group, the pharmaceutically-acceptable base-addition salts thereof.

In the above formula I and throughout this specification, the amino-acid residues are designated by their standard abbreviations (*Pure and Applied Chemistry*, 1974, 40, 317–331). Where the configuration of a particular amino-acid is not designated, that amino-acid (apart from glycine which contains no asymmetric centre) has the natural L-configuration.

A particular group of compounds within the above definition is that wherein A is D-Ala or D-Ser and G is Gly-Gln or a direct bond.

A preferred group of compounds within the above definition is that wherein A is D-Ala, B is Leu, E is Val, F is His and G is Gly-Gln.

The preferred compound of the invention is that wherein A is D-Ala, B is Leu, E is Val, F is His, G is Gly-Gln and H is a hydroxy radical.

A particular pharmaceutically-acceptable acid-addition salt of the invention is, for example, a hydrochloride, phosphate, citrate, acetate or trifluoroacetate.

A particular pharmaceutically-acceptable base-addition salt of the invention is, for example, an ammonium or meglumine salt.

The polypeptide of the invention may be manufactured by methods known in themselves for the manufacture of chemically analogous compounds. Thus the following processes, A, B, E, F, G and K having the meanings stated above, are provided as further features of the invention:

(a) the removal of one or more conventional peptide protecting groups from a protected polypeptide to give the compound of the formula I; or (b) for those compounds in which K is an amino or alkoxy radical, reaction of the carboxylic acid having the formula I given in claim 1 in which K is a hydroxy radical, or an activated derivative thereof, with ammonia or an alcohol of 1 to 6 carbon atoms.

In process (a) the deprotection process may involve removal from a resin used in solid-phase synthesis according to Merrifield (R. B. Merrifield, *Advances in Enzymology*, 1969, 32, 221) or alternatively may involve removal of one or more of the standard protecting groups employed in peptide chemistry (see for example M. Bodansky and M. A. Ondetti, "Peptide Synthesis", Interscience, New York, 1966, Chapter IV.

In process (b) a suitable activated derivative of the starting material is, for example, an ester or anhydride. In the case of the activated derivative, the reaction may be conducted by bringing the activated derivative into contact with ammonia or the appropriate alcohol in the presence of a diluent or solvent. In those cases in which the starting material is the free acid, the reaction with ammonia or the appropriate alcohol may be brought about by a standard peptide coupling reagent such as N,N'-dicyclohexylcarbodi-imide.

The starting materials for use in the processes of the invention may be prepared from known compounds by standard peptide coupling reactions, standard peptide protection reactions and standard peptide deprotection reactions will known to one skilled in this art. The starting materials are most conveniently prepared by Merrifield solid phase synthesis, for example as set out in the Example.

As noted above, the compound of the formula I has analgesic activity in warm-blooded animals. This may be demonstrated in a standard test for detecting analgesic activity such as the mouse hot-plate test (Eddy and Leimbach, *J. Pharmac. Exp. Therap.*, 1953, 107, 385–393). This test is carried out as follows. Groups of three female mice each weighing 22 to 25g. are used to test each compound. Each mouse is placed on a heated thermostatically-controlled copper surface at 56° C., and the time taken to react to the thermal stimulus (for example by licking its hind paws) is recorded. Normal reaction times are in the range of 3 to 5 seconds.

Each of the three mice is then dosed intravenously with 100 mg./kg. of a solution of the test compound. At 5, 10 and 30 minutes after dosing, each mouse is again placed on the hot plate and its reaction time determined. If the mouse does not respond after 20 seconds, the mouse is removed from the hot plate. In this circumstance the compound is regarded as having maximum activity at this dose.

A compound producing a mean increase in reaction time of at least three seconds is regarded as active. An active compound is then retested at lower doses.

The compound of the formula I in which A is D-Ala, B is Leu, E is Val, F is His, G is Gly-Gln and H is a hydroxy radical produces a mean increase in reaction time of 15 seconds at 100 mg./kg., and a mean increase in reaction time of 6 seconds at 25 mg./kg. At 100 mg./kg., the duration of analgesic effect is at least 3 hours, and there are no obvious signs of toxicity.

According to a further feature of the invention there is provided a pharmaceutical composition which comprises as active ingredient the polypeptide derivative of the invention in association with a non-toxic pharmaceutically-acceptable diluent or carrier.

The pharmaceutical composition may be, for example, in a form suitable for parenteral administration, for which purposes it may be formulated by means known to the art into the form of sterile injectable aqueous or oily solutions or suspensions.

The pharmaceutical composition of the invention may also contain, in addition to the polypeptide derivative, one or more known drugs selected from other analgesic agents, for example aspirin, paracetamol, phenacetin, codeine, pethidine, and morphine, anti-inflammatory agents, for example naproxen, indomethacin and ibuprofen, neuroleptic agents such as chlorpromazine, prochlorperazine, trifluoperazine and haloperidol and other sedative drugs and tranquillisers such as chlordiazepoxide, phenobarbitone and amylobarbitone.

A preferred pharmaceutical composition of the invention is one suitable for intravenous, intramuscular or subcutaneous injection, for example a sterile aqueous solution containing between 1 and 50 mg./ml. of active ingredient.

The pharmaceutical composition of the invention will normally be administered to man for the treatment or prevention of pain at such a dose that each patient receives an intramuscular or subcutaneous dose of between 2 and 150 mg. of active ingredient or an intravenous dose of between 1 and 100 mg. of active ingredient.

The composition may be administered according to a regime determined by the biological half-life of the polypeptide derivative, for example at intervals of from 0.5 to 4 times the biological half-line, for example 2 to 6 times per day. The composition of the invention will be of particular use in alleviating the pain experienced during and immediately after a surgical operation, and in this situation will normally be administered during the operation itself and in the immediate post-operative period.

The injectable composition of the invention may be administered by slug dose, either directly into the site of injection or into a previously-placed intravenous infusion arrangement, or it may be administered more slowly in dilute solution as a component of the intravenous infusion fluid.

The invention is illustrated, but not limited by the following Example:

In the following Example $R_f$ refers to ascending thin layer chromatography on silica gel plates ("Kieselgel" G). The solvent systems used in this chromatography were butan-1-ol/acetic acid/water (4:1:5 v/v)($R_fA$), butan-1-ol/acetic acid/water/pyridine (15:3:12:10 v/v)($R_fB$), butan-2-ol/3% w/v aqueous ammonium hydroxide (3:1 v/v)($R_fC$), acetonitrile/water (3:1 v/v) ($R_fD$), chloroform/ethanol (1:4 v/v)($R_fF$), cyclohexane/ethyl acetate/methanol (1:1:1 v/v)($R_fH$), chloroform/methanol/water (11:8:2 v/v)($R_fK$), chloroform/methanol (19:1 v/v)($R_fP$), chloroform/methanol (9:1 v/v)($R_fQ$), chloroform/methanol/acetic acid (95:5:0.5 v/v)($R_fR$) and chloroform/methanol/acetic acid (90:10:1 v/v)($R_fS$). In all cases, plates were examined under U.V. light and treated with fluorescamine, ninhydrin, and chlorine-starch-iodide reagents. Unless otherwise stated, the quoting of an $R_f$ implies that a single spot was revealed by these methods.

The following abbreviations are used in the Example:
TFA = trifluoroacetic acid
TEA = triethylamine
DMF = dimethylformamide
DCCI = N,N'-dicyclohexylcarbodi-imide
ONp = p-nitrophenyl ester
Bzl = benzyl
$Bu^t$ = t-butyl
BOC = t-butoxycarbonyl "Sephadex", "Biogel", "BioRex" and "Kieselgel" are Trade Marks.

EXAMPLE

H-Tyr-D-Ala-Gly-Phe-Leu-Thr-Ser-Glu-Lys-Ser-Gln-Thr-Pro-Leu-Val-Thr-Leu-Phe-Lys-Asn-Ala-Ile-Val-Lys-Asn-Ala-His-Lys-Lys-Gly-Gln-OH

N-t-Butoxycarbonyl-O-t-butyl-L-tyrosyl-D-alanylglycyl-L-phenylalanyl-L-leucyl-O-benzyl-L-threonyl-O-benzyl-L-seryl-O-benzyl-L-glutamyl-$N^\epsilon$-2,4-dichlorobenzyloxycarbonyl-L-lysyl-O-benzyl-L-seryl-L-glutaminyl-O-benzyl-L-threonyl-L-prolyl-L-leucyl-L-valyl-O-benzyl-L-threonyl-L-leucyl-L-phenylalanyl-$N^\epsilon$-2,4-dichlorobenzyloxycarbonyl-L-lysyl-L-asparaginyl-L-alanyl-L-isoleucyl-L-valyl-$N^\epsilon$-2,4-dichlorobenzyloxycarbonyl-L-lysyl-L-asparaginyl-L-alanyl-N-toluene-p-sulphonyl-L-histidyl-$N^\epsilon$-2,4-dichlorobenzyloxycarbonyl-L-lysyl-$N^\epsilon$-2,4-dichlorobenzyloxycarbonyl-L-lysylglycyl-L-glutaminyl-polystyrene resin (4 g.) was treated in vacuo with liquid anhydrous hydrogen fluoride (36 ml.) and anisole (4 ml.) at 0° C. for 30 minutes. The hydrogen fluoride and anisole were then removed as quickly as possible by evaporation under reduced pressure at 0° C. and the residue was extracted with ether and then with trifluoroacetic acid. The trifluoroacetic acid extract was evaporated to dryness and the residue taken up in 10% v/v aqueous acetic acid and freeze-dried. The resulting crude peptide was purified by column chromatography using (a) G10 "Sephadex" in 10% v/v aqueous acetic acid (molecular sieving), (b) G25 "Sephadex" in 10% v/v aqueous acetic acid (molecular sieving), (c) P6 "Biogel" in 0.05M aqueous ammonium acetate (molecular sieving) and finally (d) "BioRex" 70 in water containing an increasing amount, up to 25% v/v, of acetic acid (cation exchange).

The product had $R_fB$ 0.48 (with tailing) and produced a mean increase in reaction time on the mouse hot-plate test of 15 seconds at an intravenous dose of 100 mg./kg.

The protected 31 member polypeptide-polystyrene resin used as starting material may be obtained as follows:

Solid phase synthesis

Chlorinated polystyrene resin (Lab. System Inc. Batch No. LS601) (4 g.; chlorine content 0.75 mmole/g., 1% cross linked with divinylbenzene) was heated under reflux in ethanol (30 ml.) in a 250 ml. round bottom flask with t-butoxycarbonyl-L-glutamine (0.735 g.; 3 mmole) and triethylamine (0.373 ml.; 2.7 mmole) for 24 hours. The resin was filtered and washed with ethanol, methanol and methylene chloride. The resin was found to be substituted to the extent of 0.15 mmole of t-butoxycarbonyl-L-glutamine per gram of resin by amino-acid analysis.

The resin was transferred to the reaction vessel (10 g. capacity) of a Beckman Model 990 Peptide Synthesiser. The following programmed operations were then carried out:

1. Wash with $CH_2Cl_2$ for 1 minute: 3 times.
2. Prewash with 25% v/v TFA in $CH_2Cl_2$ for 1 minute: 3 times.

3. Deprotect with 25% v/v TFA in CH$_2$Cl$_2$ for 30 minutes: once.
4. Wash with CH$_2$Cl$_2$ for 1 minute: 5 times.
5. Wash with i-PrOH for 1 minute: twice.
6. Wash with CH$_2$Cl$_2$ for 1 minute: 3 times.
7. Prewash with 10% v/v TEA in CH$_2$Cl$_2$ for 1 minute: once.
8. Neutralise with 10% v/v TEA in CH$_2$Cl$_2$ for 5 minutes: once.
9. Wash with CH$_2$Cl$_2$ for 1 minute: 3 times.
10. Wash with i-PrOH for 1 minute: twice.
11. Wash with CH$_2$Cl$_2$ for 1 minute: 3 times.
12. Add BOC-Gly-OH (2.5 equivalents based on initial glutamine incorporation) in CH$_2$Cl$_2$ and stir for 5 minutes.
13. Add DCCI (2.5 equivalents in CH$_2$Cl$_2$) and couple for 1 hour.
14. Wash with CH$_2$Cl$_2$ for 1 minute: 4 times.
15–21. As operations 5–11.
22. Add BOC-Gly-OH (2.5 equivalents) in DMF-CH$_2$Cl$_2$ and stir for 5 minutes.
23. Add DCCI (2.5 equivalents) in CH$_2$Cl$_2$ (to give 1:1 DMF-CH$_2$Cl$_2$) and stir for 3 hours.
24. As operation 14.

Further amino-acids were then incorporated into the resin by, in each case, repeating the above 24 operations, but using the appropriate BOC-amino-acid or BOC-amino-acid derivative in stages 12 and 22 in place of BOC-Gly-OH. When Asn or Gln were being incorporated, solutions of BOC-Asn-ONp or BOC-Gln-ONp (5 equivalents) and 1-hydroxybenzotriazole (5 equivalents) in DMF were used in operations 12 and 22, and stirring was continued for 4 hours in operation 12, and for 8 hours in operation 22; in these cases operations 13 and 23 were omitted. The degree of coupling during each incorporation of an amino-acid was monitored by the ninhydrin test (Kaiser et al., *Analytical Biochemistry,* 1970, 34, 595) and by the fluorescamine test (Felix and Jimenez, *Analytical Biochemistry,* 1973, 52, 377).

The BOC-amino-acids or BOC-amino-acid derivatives used, and the order in which they were incorporated were as follows:

N$^\alpha$-BOC-N$^\epsilon$-2,4-dichlorobenzyloxycarbonyl-L-lysine;
N$^\alpha$-BOC-N$^\epsilon$-2,4-dichlorobenzyloxycarbonyl-L-lysine;
N$^\alpha$-BOC-N$^{im}$-toluene-p-sulphonyl-L-histidine;
BOC-Ala-OH;
BOC-Asn-ONp;
N$^\alpha$-BOC-N$^\epsilon$-2,4-dichlorobenzyloxycarbonyl-L-lysine
BOC-Val-OH;
BOC-Ile-OH;
BOC-Ala-OH;
BOC-Asn-ONp;
N$^\alpha$-BOC-N$^\epsilon$-2,4-dichlorobenzyloxycarbonyl-L-lysine;
BOC-Phe-OH;
BOC-Leu-OH;
BOC-Thr(Bzl)-OH;
BOC-Val-OH;
BOC-Leu-OH;
BOC-Pro-OH;
BOC-Thr(Bzl)-OH;
BOC-Gln-ONp;
BOC-Ser(Bzl)-OH;
N$^\alpha$-BOC-N$^\epsilon$-2,4-dichlorobenzyloxycarbonyl-L-lysine;
BOC-Glu(OBzl)-OH;
BOC-Ser(Bzl)-OH;
BOC-Thr(Bzl)-OH;
BOC-Tyr(Bu$^t$)-D-Ala-Gly-Phe-Leu-OH.

In the case of incorporation of the final pentapeptide fragment (whose preparation is described as starting material number 161 in Example 94 in U.K. Patent Application No. 14362/76), the pentapeptide fragment (1.2 equivalents), 1-hydroxybenzotriazole and N-methylmorpholine (2.4 equivalents each) were used in stages 12 and 22, DMF (1 ml.) was used to dissolve the 1-hydroxybenzotriazole in stage 12, and stirring was continued for 20 minutes in stages 12 and 22, and for 24 hours in stages 13 and 23.

The final protected 31 member polypeptide coupled to the resin was washed with dimethylformamide, methylene chloride, isopropanol, and dried in vacuo.

What we claim is:
1. A polypeptide of the formula:

H-Tyr-A-Gly-Phe-B-Thr-Ser-Glu-Lys-Ser-Gln-Thr-Pro-Leu-Val-Thr-Leu-Phe-Lys-Asn-Ala-Ile-E-Lys-Asn-Ala-F-Lys-Lys-G-K        I in which A is selected from the group consisting of D-Ala, D-Ser and D-Met, B is selected from the group consisting of Leu and Met, E is selected from the group consisting of Val and Ile, F is selected from the group consisting of His and Tyr, G is selected from the group consisting of Gly-Gln, Gly-Glu and a direct bond, and K is selected from the group consisting of a hydroxy radical, an amino radical and an alkoxy radical of 1 to 6 carbons; and the pharmaceutically-acceptable acid-addition salts thereof, and, where the polypeptide of the formula I contains a free carboxy group, the pharmaceutically-acceptable base-addition salts thereof.

2. A polypeptide as claimed in claim 1 in which A is D-Ala or D-Ser and G is Gly-Gln or a direct bond.

3. A polypeptide as claimed in claim 1 in which A is D-Ala, B is Leu, E is Val, F is His and G is Gly-Gln.

4. A polypeptide as claimed in claim 3 in which K is a hydroxy radical.

5. An analgesic pharmaceutical composition which comprises as active ingredient an effective amount of a polypeptide as claimed in claim 1 in association with a major amount of a non-toxic pharmaceutically-acceptable diluent or carrier.

6. A composition as claimed in claim 5 which is in a form suitable for parenteral administration.

7. A method of producing analgesia in warm-blooded animals including man which comprises administering an analgesically-effective amount of a polypeptide as claimed in claim 1.

* * * * *